United States Patent
Shipp

(10) Patent No.: US 8,216,272 B2
(45) Date of Patent: *Jul. 10, 2012

(54) ABSORBABLE ANCHOR FOR HERNIA MESH FIXATION

(75) Inventor: John I. Shipp, Atlantic Beach, FL (US)

(73) Assignee: Tyco Healthcare Group LP, Mansfield, MA (US)

( * ) Notice: Subject to any disclaimer, the term of this patent is extended or adjusted under 35 U.S.C. 154(b) by 89 days.

This patent is subject to a terminal disclaimer.

(21) Appl. No.: 12/959,435

(22) Filed: Dec. 3, 2010

(65) Prior Publication Data

US 2011/0071556 A1    Mar. 24, 2011

Related U.S. Application Data

(63) Continuation of application No. 10/907,834, filed on Apr. 18, 2005, now Pat. No. 8,114,099, which is a continuation-in-part of application No. 10/905,020, filed on Dec. 10, 2004, now abandoned, and a continuation-in-part of application No. 10/709,297, filed on Apr. 27, 2004, now Pat. No. 7,758,612.

(51) Int. Cl.
*A61B 17/08* (2006.01)
(52) U.S. Cl. .......... 606/219; 606/142; 606/143
(58) Field of Classification Search .......... 606/295, 606/301, 305, 312, 316, 151, 213, 157, 158
See application file for complete search history.

(56) References Cited

U.S. PATENT DOCUMENTS

| | | |
|---|---|---|
| 4,756,653 A | 7/1988 | Berger |
| 4,824,865 A | 4/1989 | Bowser et al. |
| 4,884,572 A | 12/1989 | Bays et al. |
| 4,895,148 A | 1/1990 | Bays et al. |
| 4,976,715 A | 11/1990 | Bays et al. |
| 5,059,206 A | 10/1991 | Wornters |
| 5,080,665 A | 1/1992 | Jarrett et al. |
| 5,129,906 A | 7/1992 | Ross et al. |
| 5,169,400 A | 12/1992 | Muhling et al. |
| 5,259,398 A | 11/1993 | Vrespa |
| 5,354,292 A | 8/1994 | Braeuer et al. |
| 5,364,400 A | 11/1994 | Rego et al. |
| 5,582,616 A | 12/1996 | Bolduc et al. |
| 5,643,320 A | 7/1997 | Lower et al. |
| 5,730,744 A | 3/1998 | Justin et al. |
| 5,810,882 A | 9/1998 | Bolduc et al. |
| 5,824,008 A | 10/1998 | Bolduc et al. |
| 5,830,221 A | 11/1998 | Stein et al. |
| 5,891,146 A | 4/1999 | Simon et al. |

(Continued)

FOREIGN PATENT DOCUMENTS

EP         0 199 037 A2   10/1986

(Continued)

*Primary Examiner* — Tuan V Nguyen

(57) ABSTRACT

A delivery device for delivering at least one surgical anchor into a patient's tissue is provided and includes a housing; a delivery tube with distal and proximal ends, the delivery tube including a retention member disposed at the distal end thereof and extending inwardly at an angle transverse with respect to a longitudinal axis of the delivery tube; and a reciprocating anchor carrier with distal and proximal positions and distal and proximal ends, the distal end of the anchor carrier terminating in a tissue penetrator member, the anchor carrier being moveable distally and proximally with respect to the delivery device, the tissue penetrator member defining an annular shoulder configured to removably retain a plurality of surgical anchors about the anchor carrier.

11 Claims, 13 Drawing Sheets

U.S. PATENT DOCUMENTS

| | | | |
|---|---|---|---|
| 5,971,985 | A | 8/1999 | Carchidi et al. |
| 5,954,722 | A | 9/1999 | Bono |
| 5,964,772 | A | 10/1999 | Bolduc et al. |
| 6,030,162 | A | 2/2000 | Huebner |
| 6,096,060 | A | 8/2000 | Fitts et al. |
| 6,296,656 | B1 | 10/2001 | Bolduc et al. |
| 6,306,140 | B1 | 10/2001 | Dissiqui |
| 6,319,270 | B1 | 11/2001 | Grafton |
| 6,533,454 | B1 | 3/2003 | Kaikkonen et al. |
| 6,562,051 | B1 | 5/2003 | Bolduc et al. |
| 6,747,121 | B2 | 6/2004 | Gogolewski |
| 6,884,248 | B2 | 4/2005 | Bolduc et al. |
| 6,955,677 | B2 | 10/2005 | Dahners |
| 7,758,612 | B2 * | 7/2010 | Shipp .............................. 606/219 |
| 2001/0004694 | A1 | 6/2001 | Carchidi et al. |
| 2001/0007074 | A1 | 7/2001 | Strobel et al. |
| 2002/0004660 | A1 | 1/2002 | Henniges et al. |
| 2002/0013605 | A1 | 1/2002 | Bolduc et al. |
| 2003/0120292 | A1 * | 6/2003 | Park et al. ..................... 606/153 |
| 2003/0135226 | A1 | 7/2003 | Bolduc et al. |
| 2004/0073218 | A1 | 4/2004 | Dahners |
| 2004/0098045 | A1 | 5/2004 | Grafton et al. |
| 2004/0153101 | A1 | 8/2004 | Bolduc et al. |
| 2004/0204723 | A1 | 10/2004 | Kayan |
| 2005/0136764 | A1 | 6/2005 | Sherman |
| 2005/0171562 | A1 | 8/2005 | Criscuolo et al. |
| 2005/0267478 | A1 | 12/2005 | Corradi et al. |
| 2008/0097523 | A1 | 4/2008 | Bolduc et al. |

FOREIGN PATENT DOCUMENTS

| | | |
|---|---|---|
| EP | 1025803 | 8/2000 |
| EP | 1293168 | 3/2003 |
| EP | 2005975 A2 | 12/2008 |
| JP | 09149906 | 6/1997 |
| WO | WO 98/11814 A2 | 3/1998 |
| WO | WO 01/62136 | 8/2001 |
| WO | WO 01/97677 | 12/2001 |
| WO | WO 02/091932 | 11/2002 |
| WO | WO 03/034925 | 5/2003 |
| WO | WO 03/103507 | 12/2003 |

* cited by examiner

ABSORBABLE ANCHOR FOR HERNIA MESH FIXATION

CROSS-REFERENCE TO RELATED APPLICATIONS

The present application is a Continuation Application claiming the benefit of and priority to U.S. patent application Ser. No. 10/907,834, filed on Apr. 18, 2005, now U.S. Pat. No. 8,114,099, which is a Continuation-in-Part Application claiming the benefit of and priority to U.S. patent application Ser. No. 10/905,020, filed on Dec. 10, 2004 (now abandoned), and a Continuation-in-Part Application claiming the benefit of and priority to U.S. patent application Ser. No. 10/709,297 filed on Apr. 27, 2004, now U.S. Pat. No. 7,758,612, the entire contents of which are hereby incorporated by reference.

BACKGROUND OF THE INVENTION

This invention relates to surgical fasteners and their associated applicators, and more particularly, surgically fastening material to tissue and their method of use.

In laparoscopic repair of hernias surgical fasteners have been used to attach repair mesh over the hernia defect so that bowel and other abdominal tissue are blocked from forming an external bulge that is typical of abdominal hernias. The role of the fasteners is to keep the mesh in proper position until tissue ingrowth is adequate to hold the mesh in place under various internal and external conditions. Adequate ingrowth usually takes place in 6-8 weeks. After that time the fasteners play no therapeutic role. Fixation anchors comprise a mesh fixation feature, or head, a mesh-tissue interface section, and a tissue-snaring feature that holds the anchor in place under force developed inside or outside the body.

Meanwhile, an inguinal hernia is formed when small a loop of bowel or intestine protrudes through a weak place or defect within the lower abdominal muscle wall or groin. This condition is rather common, particularly in males. Hernias of this type can be a congenital defect or can be caused by straining or lifting heavy objects. The protrusion results in an unsightly bulge in the groin area often causing pain, reduced lifting ability, and in some cases, impaction of the bowel.

Surgery is a common solution to an inguinal hernia. The preferred surgical technique requires extracting the bowel from the defect, placing a surgical prosthesis such as a mesh patch over the open defect, and attaching the mesh patch to the inguinal floor with conventional sutures or with surgical fasteners or anchors. The repair is accomplished using either open or laparoscopic surgery. Surgical anchors are routinely used in the laparoscopic procedures owing to the difficulty in suturing under laparoscopic conditions.

At present, there are a variety of surgical devices and fasteners available for the surgeon to use in endoscopic and open procedures to attach the mesh patch to the inguinal floor or abdominal wall. One such mesh attachment instrument uses a helical wire fastener formed in the shape of a helical compression spring. Multiple helical wire fasteners are stored serially within the 5 mm shaft, and are screwed or rotated into the mesh and the overlaid tissue to form the anchor for the prosthesis. A load spring is used to bias or feed the plurality of helical fasteners distally within the shaft. A protrusion extends into the shaft, while preventing the ejection of the stack of fasteners by the load spring, allows passage of the rotating fastener. U.S. Pat. Nos. 5,582,616 and 5,810,882 by Lee Bolduc, and U.S. Pat. No. 5,830,221 by Jeffrey Stein describe instruments and fasteners of this type.

U.S. Pat. Nos. 5,203,864 and 5,290,297 by Phillips describe two embodiments of a hernia fastener and delivery devices. One of the Phillips fasteners is formed in the shape of a unidirectional dart with flexible anchor members. The dart is forced through the mesh and into tissue by a drive rod urged distally by the surgeon's thumb. The anchor members are forced inward until the distal end of the dart penetrates the overlaid tissue and then the anchor members, presumably, expand outward without any proximal force on the dart thus forming an anchor arrangement. This requires an extremely forceful spring force generated by the anchor members. Multiple darts are stored in a rotating cylinder, much like a revolver handgun.

Phillips second fastener embodiment is a flexible H shaped device. The tissue penetrating means is a hollow needle containing one of the legs of the H. The H shape is flattened with the cross member and the other leg remaining outside the hollow needle owing to a longitudinal slot therein. A drive rod urged distally by the surgeon's thumb again delivers the fastener. The contained leg of the H penetrates the mesh and tissue. After ejection the fastener presumably returns to the equilibrium H shape with one leg below the tissue and one leg in contact with the mesh with the cross member penetrating the mesh and the tissue, similar to some plastic clothing tag attachments. Phillips depicts the installed device returning to the H shape but he fails to teach how to generate enough spring action from the device to overcome the high radial forces generated by the tissue.

A series of patents, U.S. Pat. Nos. 6,572,626, 6,551,333, 6,447,524, and 6,425,900 and patent applications 200200877170 and 20020068947 by Kuhns and Kodel, all assigned to Ethicon, describe super elastic, or shape metal fasteners and a delivery mechanism for them. The fasteners are stored in the delivery device in a smaller state and upon insertion into the mesh and tissue, transitions to a larger anchor shaped state. The Ethicon fastener is delivered by an elaborate multistage mechanism through a hollow needle that has penetrated the mesh and the tissue. The hollow needle is then retracted to leave the fastener to change shape to a more suitable configuration for holding the mesh in place.

The primary problem with these prior art fasteners is that the mesh is attached to body tissue in as many as 100 places for large ventral hernias. This results in a large quantity of metal remaining in the body as permanent implants, even though after the ingrowth phase the fasteners serve no useful purpose. Compounding this problem the distal ends of the fasteners are sharp pointed and thus pose a continued pain or nerve damage hazard.

One alternative to metallic fixation devices is bio-absorbable materials. These materials are degraded in the body by hydrolysis. After degradation the body metabolizes them as carbon dioxide and water. These materials require special attention to many design details that are much more demanding than their counterparts in metallic fixation devices such as applicator tool design, sterilization processes, and packaging. Metallic tacks or anchors provide structural strength that simplifies their insertion and since the materials, usually titanium or nickel-titanium alloys (shape metal), are chemical and radiation resistant and are very temperature tolerant many options are available to the designer. Not so for bio-absorbable materials.

The basic considerations of an effective mesh fixation applicator and absorbable anchor are the material strength, absorption time, the sterilization method, and packaging requirements, the ease of insertion of the anchor through the mesh and into the tissue, the ease of ejecting the anchor from the tool, the fixation strength of the anchor once implanted, the time required after insertion for the anchor to be degraded and metabolized by the body are all effected by the choice of anchor material, the geometry of the design, and the forming process.

Materials of appropriate strength are generally limited to synthetic materials. Currently, the U.S. FDA has cleared devices made from polyglycolide (PG), polylactide (PL), poly caprolactone, poly dioxanone, trimethylene carbonate, and some of their co-polymers for implant in the human body. These materials and their co-polymers exhibit a wide variation of properties. Flex modulus ranges from a few thousand to a few million PSI, tensile strength ranges from 1000 to 20,000 PSI, in vivo absorption times range from a few days to more than two years, glass transition temperatures range from 30-65 degrees centigrade, all with acceptable bio-responses. Unfortunately, however, the optimum values of each of these properties are not available in any one of these materials so that it is necessary to make performance tradeoffs.

Mechanical Properties

Most hernia mesh fixation devices are currently used in laparoscopic hernia repair. In general laparoscopic entry ports have been standardized to either 5 or 10 mm (nominal) diameter. In the case of prior art of metallic fixation devices 5 mm applicators are universally employed. Since it is not clear that the medical advantages of the use of absorbable anchors would totally out weigh the disadvantages of moving to a 10 mm applicator it must be assumed that absorbable anchors must also employ 5 mm applicators. Because of the lower strength of absorbable material this requirement imposes severe design constraints on both the applier and the anchor.

After successful insertion there are two ways for a fixation anchor to fail. It can fracture, separating the mesh holding feature from the tissue-snaring feature, or it can pull out of the tissue owing to inadequate tissue snaring. Increased forces are placed on the anchor during sudden elevations of intra-abdominal pressure (IAP) caused by straining, coughing or the Valsalva maneuver, a medical procedure whereby patients close their nose and mouth and forcibly exhale to test for certain heart conditions. The later can generate an IAP of up to 6.5 PSI. For nonporous mesh and a hernia area of 50 square centimeters, for example this increased IAP places 50.3 pounds of force on the anchors fixating the mesh. Typically 40 anchors would be used to secure the hernia mesh of 150 square centimeters so that each anchor would, at this elevated IAP, experience approximately a 1.26-pound tensile force on the mesh-retaining feature and the tissue-snare feature. The tensile strength between these two features and the tissue snare force must exceed this force generated by the increased IAP or else the mesh fixation can fail.

The strength and flexibility of the anchor material are of major importance in the design considerations of the applicator, particularly in the case of anchors formed from polymers. Ory, et al (U.S. Pat. No. 6,692,506) teaches the use of L Lactic Acid polymer. Ory discloses adequate fixation strengths but the applicator device required to insert his anchor is necessarily 10 mm in diameter thereby causing the procedure to be more invasive than necessary. Ory further discloses a hollow needle with a large outside diameter, through which the anchor is inserted, that forms a rather large hole in the mesh and tissue to supply adequate columnar strength for penetration of the anchor. Entry holes of this size can give rise to multiple small hernias know as Swiss cheese hernias.

Absorption Time

There are two forms of PL, one synthesized from the d optical isomer and the other from the l optical isomer. These are sometimes designated DPL and LPL. A polymer with 50-50 random mixture of L and D is herein designated DLPL.

High molecular weight homo and co-polymers of PG and PL exhibit absorption times ranging from 1 month to greater than 24 months. Homo crystalline PG and PL generally require greater than 6 months to absorb and thus are not optimum materials for hernia mesh fixation. Amorphous co-polymers of PG and PL, on the other hand, typically degrade in less than 6 months and are preferably used in the present invention. For high molecular weight co-polymers of PG and PL the actual absorption time is dependent on the molar ratio and the residual monomer content. For a given monomer residual the absorption time varies from about 1 month to about 5 months as the molar content of DLPL increases from 50 to 85 percent with PG decreasing from 50 to 15 percent. Co-polymers of DLPL and PG in the molar range of 50 to 85 percent of DLPL are preferred for this invention. The geometry of the anchor also effects the absorption time. Smaller high surface area devices absorb faster.

The time required for the human body to react to the foreign body of the mesh for tissue ingrowth into the mesh is typically 10 days. However, mesh migration and mesh contraction can occur for more than two months if not adequately stabilized. Since fixation anchors can impinge upon nerves and cause pain it is desirable for the anchors to be absorbed as soon as possible after the tissue ingrowth and after the mesh is secure against migration or contraction. For most absorbable materials there is a difference between the time for loss of fixation strength and mass loss. Fixation strength decreases quicker than anchor mass owing to some degree of crystalline structure in the polymer. For these reasons the preferred absorption time for the current invention is 3-5 months after implant.

Temperature Effects

Glass transition temperature (Tg) is the temperature above which a polymer becomes soft, can loose its shape, and upon re-cooling can shrink considerably. Both crystalline and amorphous polymers exhibit glass transitions in a temperature range that depends on the mobility of the molecules, which is effected by a number of factors such as molecular weight and the amount of residual monomers. Glass transition temperatures range from about 43 to 55 degrees centigrade (deg. C.) for co-polymers of PG and DLPL. Where as 100% PG has a Tg of 35-40 deg. C. and 100% PL exhibits a Tg from 50-60 deg. C. Since the core temperature of the body can reach 40 degrees C. the preferred Tg for the material comprising the current invention is greater than 40 deg. C. In addition hernia mesh anchors are often manufactured and shipped via surface transportation under uncontrolled, extreme heat conditions. Temperatures in commercial shipping compartments in the summer can exceed 60 degrees C. It is necessary then to provide thermal protection in the packaging so that the anchor temperature does not exceed its Tg.

Sterilization and Packaging

Bio-absorbable polymers degrade when exposed to high humidity and temperature. Autoclaving cannot be used, for example. Most ethylene oxide (ETO) sterilization processes employ steam and high temperatures (above Tg) to obtain reasonable "kill" times for the bio-burden commonly found on the device. High doses of gamma radiation or electron beam radiation (E Bream), both accepted methods of sterilization for many devices, could weaken the mechanical properties of PG, PL and their co-polymers. It is therefore necessary during the manufacturing process of the anchor and its applicator to maintain cleanliness to a high degree such that the bio-burden of the components is small enough so that pathogens are adequately eradicated with less severe forms of sterilization.

Radiation doses above 25 kilogray (kgy) are known to lessen the mechanical strength of bio-absorbable polymers whereas some pathogens are known to resist radiation doses below 10 kgy. It is therefore necessary, for the preferred embodiment of the present invention during manufacturing to keep the pathogen count below a certain threshold to insure the accepted regulatory standards are met for radiation levels between 10 and 25 kgy.

In a second embodiment of the present invention it is necessary during manufacturing to keep the pathogen count below a certain threshold to insure the accepted regulatory standards are obtained for sterilization using a non-steam, low temperature, ethylene oxide (ETO) process below Tg of the anchor polymer.

Anchors of the present invention must be carefully packaged to maintain adequate shelf life prior to use. Care must be taken to hermetically seal the device and to either vacuum pack, flood the package with a non-reactive dry gas prior to sealing, or to pack the device with a desiccant to absorb any water vapor since hydrolysis breaks down the backbone of the co-polymers.

ETO sterilization requires the gas to contact the device to be sterilized. Devices that are not humidity sensitive can be packaged in a breathable packaging material so that ETO can diffuse in, and after sterilization, diffuse out so that the device can be sterilized without unsealing the packaging. For the alternate embodiment of the present invention the device must be hermetically sealed after sterilization with ETO. Since gamma radiation and electron beam radiation sterilization can be accomplished through hermetically sealed packaging without disturbing the seal, either of these two sterilization processes is employed for the preferred embodiment of the present invention.

Ory, et al (U.S. Pat. No. 6,692,506), Criscuolo, et al (US application 20040092937), Phillips (U.S. Pat. Nos. 5,203,864 and 5,290,297), Kayan (U.S. application 20040204723), and Shipp (U.S. application Ser. Nos. 10/709,297 and 10/905,020) have suggested the use of bio-absorbable materials for use as hernia mesh fixation devices to solve the problems associated with the permanency of metal implants. Ory, preferably, suggests forming the fixation device from LPL but the absorption time for LPL can exceed two years, much longer than optimum for hernia fixation devices since the lessening of pain depends on mass loss of the device. While Phillips and Kayan advocate the use of bio-absorbable material to form the anchor neither teach any details or methods for effectuating such a device. Criscuolo suggests the use of PG and PL with an absorption time of 2-3 weeks but does not disclose a method of forming the device that results in such an absorption time. In any respect, migration and contraction of the mesh has been documented to occur up to 8 weeks after implant. Loss of fixation after 2 to 3 weeks could well lead to hernia recurrence.

Hernia mesh such as PTFE based mesh manufactured by W. L. Gore is difficult to penetrate since the material is tough, non macro-porous, and relative inelastic. Attempts to penetrate these types of meshes with a puncture type applicator result in the mesh indenting into the tissue to a significant depth prior to penetration, especially for soft tissue. This indentation sometimes allows the tissue penetrator means, often a hollow needle, to penetrate through the abdomen wall and into the surgeon's hand, thus exposing the surgeon to potential hepatitis and AIDS viruses. The anchor of the present invention is equipped with screw threads that easily penetrate tough, non macro-porous, and relative inelastic mesh with a minimum of indentation. Once the threads are screwed through the mesh the underlying tissue is pull toward the mesh by the threads rather than push away from the mesh as is the case with puncture type devices.

There are several problems associated with the prior art. The method of penetration of the helical fastener is the same as a wood screw, for example, in that the rotational thread action provides mechanical advantage for the advancement of the fastener through the mesh and tissue. The helical fastener, however, does not have a head or stop on the proximal end so that it can often be screwed all the way through the mesh and into the tissue and thus providing no fastening support for the mesh. As with any screw a pointed distal end is required to cause the screw to start into the material. This configuration can cause permanent pain for some placements of the fastener and sometimes results in the need for the fastener to be excised from the body in a subsequent surgical procedure.

Both the Phillips dart and H shape fastener must be placed in soft enough tissue that will allow the anchor members to deploy or else the holding strength is severely compromised.

The Ethicon device is very complex and expensive to manufacture owing to the delivery mechanism and the cost of the super elastic fastener material. In addition the proximal end of the fastener is not symmetric so that care must be taken to orient it correctly so that both proximal leg members contact the mesh, since fasteners are almost always deployed near the edges of the mesh. Another problem with the Ethicon device is that the delivery tube is 5 mm in diameter and the surgeon must hold a counter force with the palm of the hand on the handle to hold the delivery tube against the mesh while simultaneously applying an oppositely directed force to the trigger (actuator) with his fingers of the same hand. The trigger is spring-loaded and requires a substantially larger force than the tissue penetrating force. These forces change throughout the actuator stroke as the spring loads increase. In addition, the penetrating force peaks then suddenly decreases as the initial penetration is made. These two dynamic countervailing force requirements from the same hand sometimes causes the surgeon to apply too much handle pressure resulting in the 5 mm delivery tube puncturing the tissue causing excess bleeding and other trauma.

The distal end of the dart, the helical coil, and the shape metal fasteners are all pointed shaped and often twenty or more fasteners are used in a single case so that there are many sharply pointed fasteners that are implanted in the groin area. These fasteners can touch or penetrate nerves and cause severe pain that is more or less permanent unless they are removed in subsequent surgical procedures.

Details of the method of manufacturing the improved anchor are herein provided.

What is needed then is an absorbable mesh fixation anchor and a method of forming an absorbable mesh fixation anchor that exhibits a known absorption time and that exhibits the mechanical properties adequate for the desired fixation strength and the required implant forces.

What is also needed is a method of packaging an absorbable mesh fixation device and the delivery device that minimizes the effects of high ambient shipping temperatures and humidity.

What is also needed is a method of sterilization of an absorbable mesh fixation anchor and its delivery device that has minimal effect on their physical properties, particularly the anchor.

What is further needed then is an absorbable mesh fixation anchor of improved geometry that easily penetrates tough, non macro-porous, and relatively inelastic mesh with minimal indentation to minimize the possibility of the anchor breaching the abdominal wall.

What is needed then is a hernia mesh fastener or anchor that is simple to deploy, does not have an implanted sharp distal point, and preferably is absorbed by the body after a period of time when the tissue in-growth to the mesh obviates the need for a fastener or anchor.

What is further needed is a simple inexpensive hernia mesh anchor deployment device that does not require simultaneous dynamic countervailing force to be applied by the same hand of the surgeon.

What is still further needed then is an absorbable mesh fixation anchor of improved geometry that collapses to a smaller diameter upon penetrating the mesh and tissue to minimize the entry hole size and an absorbable mesh fixation anchor that flares out to a larger size to resist expulsion when urged proximal.

SUMMARY OF THE INVENTION

A method of producing and deploying a bio-absorbable hernia mesh fixation anchor exhibiting an in vivo absorption time between 1.5 and 13 months and its method of use is disclosed. A method of sterilization and a method of packaging the anchor to retain the critical physical properties of the anchor prior to implantation are also disclosed. The hernia mesh fixation device of the present invention is, preferably, injection molded using any of a variety of mole fractions of d, l-lactide and glycolide co-polymers, depending upon the desired absorption time, and mechanical properties. Preferably the mole ratio is 75-25 percent d, l lactide to glycolide yielding an absorption time after implant of 4-5 months and a glass transition temperature of 49 Deg. C. The modulus of elasticity of the preferred embodiment is 192,000 PSI and the tensile strength is 7200 PSI after injection molding at 150 Deg. C.

The anchor of the present invention comprises a head with a threaded portion and a slotted portion, a threaded tissue-snaring section formed on a truncated body section that, upon rotation, easily penetrates tough, non macro-porous, and relative inelastic mesh and pulls underlying tissue toward the head of the anchor, firmly anchoring the mesh to the tissue and thus avoiding excessive indentation of the abdominal wall during deployment.

The anchor deliver device, or applier, of the present invention has a longitudinal axis, a handle, an actuator engaged with a rotator, an anchor retainer, an anchor advancer, a force reactor, and an anchor ejector.

Sterilization standards by the U.S. FDA allow radiation doses less than 25 kgy provided the bio-burden is below 1000 colony forming units (CFU). The components of the delivery device and the anchors of the present invention are manufactured and assembled under clean room conditions such the bio-burden is well below 1000 CFUs. This allows gamma and E Beam sterilization with doses below the damage threshold of the preferred co-polymers of DLPL and PG, 25 kgy. Mechanical properties of the injected molded anchor of the present invention have been retested after dosing with 25 kgy E Beam. The same values of flex modulus and tensile strength were measured before and after dosing. Gamma or E Beam is the preferred sterilization process, however, an alternate embodiment comprises sterilization employing ethylene oxide without the use of steam and dosed at a temperature below the glass transition temperature.

For the preferred embodiment of the present invention the delivery device loaded with anchors is first sealed into a vacuum formed tray with a breathable Tyvek (a registered trademark of DuPont) lid. This tray is then further hermetically sealed into a foil pouch. The foil pouch is then placed inside an insulated shipping container. The insulation is adequate to assure that the temperature of the anchor remains below 30 deg. C. after exposure to severe heat conditions sometimes experienced during shipping. Gamma or E Beam sterilization is accomplished by radiation through the shipping container.

In an alternate embodiment the sealed vacuum formed tray is placed into the hermetically sealed foil pouch after ETO sterilization. The ETO will penetrate the breathable lid. After the ETO process the device is sealed into the foil pouch and the pouch is placed into the thermally insulated container described above for shipping.

A delivery device for delivering a plurality of individual surgical anchors is disclosed. The delivery device comprises a housing, a delivery tube, having a distal and a proximal end, an actuator, flexible anchor reaction members, a reciprocating anchor carrier, having a distal and a proximal end and a distal and proximal position, the distal end terminating in a tissue penetrator. The device further includes at least one surgical anchor located in juxtaposition with the anchor carrier and a queuing spring to urge the anchors distally. Each of the surgical anchors has a penetration section and a head section. The surgical anchors are preferably made from an absorbable polymer. The actuator is connected to the anchor carrier and has at least two states. The first, or home state, comprises a position such that the surgical anchor is proximal the distal end of the delivery tube. The second state is such that the penetrating section of the surgical anchor is exposed beyond the distal end of the delivery tube. The anchor of the present invention is then deployed by simply applying a distal force to the handle of the housing and penetrating the prosthesis and tissue. A reaction member formed inside and affixed to the delivery tube provides a stop against which the reaction force of penetration is applied to the head section of the anchor. When the surgeon is ready to deploy the anchor, a trigger is held stationary against the handle such that no dynamic countervailing forces are encountered. The anchor has a centered internal channel through which the cylindrical anchor carrier passes. The distal penetrating tip of the anchor carrier is shaped like a conical arrowhead with a proximate step-up in diameter from the anchor carrier cylinder. The inside diameter of the distal end of the anchor closely matches the carrier cylinder diameter but allows for an easy slip fit. The proximate step-up at the penetrating tip serves as a distal stop for the anchor against the force of the queuing spring. The penetration section of the anchor is then forced through the prosthesis and tissue. The head of the anchor engages the prosthesis and thus provides a stop that does not allow the anchor to traverse the prosthesis as sometimes happens in the use of the helical fastener. The anchor of the present invention is equipped with rigid radial tissue engagement barbs. As the penetration section penetrates the tissue the rigid barbs expand the tissue to allow the section to pass into the tissue. As the proximal end of the barbs enters the tissue the expanded tissue retracts to the diameter of the penetrating section shaft thus locking the anchor in place much like an arrowhead. Unlike the flexible Phillips anchor members the rigid barbs of the present invention will not collapse in rigid tissue. The Phillips members will remain collapsed in rigid tissue thus offering little or no holding strength. After the anchor of the current invention is inserted to the head depth the surgeon releases the trigger and a restoring torsion spring places a proximal force on the anchor carrier, the distal end of the penetrating shaft of the anchor expands owing to distal longitudinal slits such that the tissue penetrator member retracts leaving the anchor in place. The process is then repeated for the next anchor.

DETAILED DESCRIPTION

Figure 1:
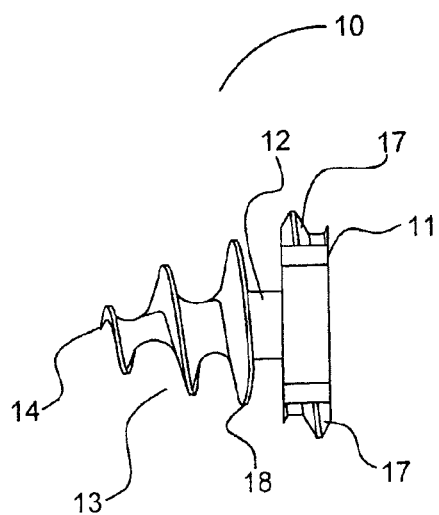
FIG. 1 is a side view of the anchor according to the present invention.
Figure 2:
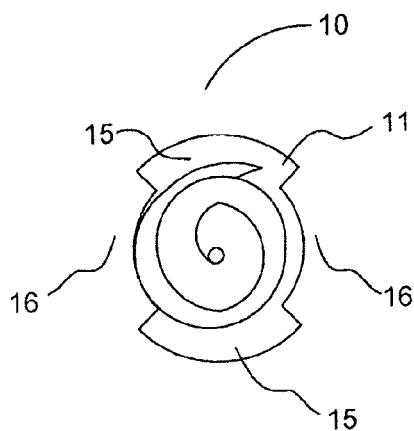
FIG. 2 is the distal end view of the anchor according to the present invention.
Figure 3:
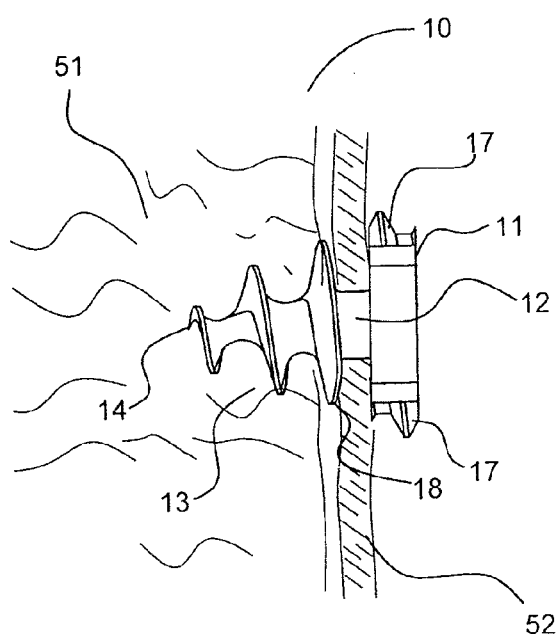
FIG. 3 depicts the anchor fixating mesh to tissue.

Turning now to FIGS. 1, 2 and 3, depictions of the anchor of the current invention, generally designated as 10. Anchor 10 comprises three sections, head section 11, mesh retention section 12, and threaded tissue-snaring section 13. Head section 11 comprises two opposing threaded sections 15 with head threads 17 and two opposing open or slotted sections 16. The distal surface of head section 11 is formed onto the proximal end of mesh retention section 12.

Mesh retention section 12 may, alternately, be tapered or right-cylinder shaped or may be omitted, which would allow the proximal end of threaded tissue-snaring section 13 to abut the distal end of head section 11. Unlike the embodiment of anchor 10 with no mesh retention section 12, either the conical or cylindrical configuration mesh retention section 12 locks mesh 52 on to anchor 10 when mesh 52 is screwed past the proximal-most tissue-snaring thread 18 since there is no thread located in mesh retention section 12 that would allow mesh 52 to be unscrewed from anchor 10. Mesh retention section 12 is generally cylindrical or conical shaped with a dimension transverse to its longitudinal axis that is smaller than the transverse dimension of head 11 and the transverse dimension of proximal most tissue-snaring thread 18.

Figure 4:
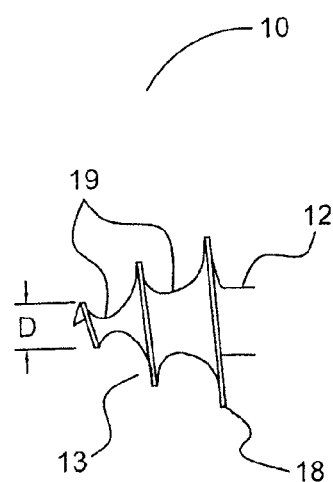
FIG. 4 depicts the shape of the tissue penetrating threads of the anchor.

Threaded tissue-snaring section 13 comprises helical threads formed onto a tapered truncated body section 19. Distal point 14 is the terminus of the distal most tissue-snaring thread. FIG. 4 is an angled view of the threaded tissue-snaring section 13 of the preferred embodiment. Body section 19 is tapered and thus becomes smaller toward the distal end of threaded tissue-snaring section 13 and terminates, or truncates, distally prior to reaching an apex. The taper can take the form of a linear taper, a convex, or a concave taper. A concave taper is preferable in that it, for a given length, yields the minimum diameter body section 19 upon truncation, preferably less than 0.01 inches. The dimension D shown in FIG. 4 is the transverse dimension of the distal most thread in the threaded tissue-snaring section 13. D should be as large as design constraints will allow, preferably greater than 0.040 inches. A small truncated body diameter and a large value of D minimizes tissue indentation. The tissue-snaring threads terminate at distal tip 14, which is distal of the truncation point of body section 19. This geometry allows for ease of mesh penetration and minimizes indentation of the mesh into soft tissue as compared to a non-truncated body with tapered threads. For a given force applied to mesh 52 by the surgeon exerting a distal force on applier 20 the larger is the dimension D the less the pressure to cause indentation of tissue 51 and mesh 52.

Figure 5:
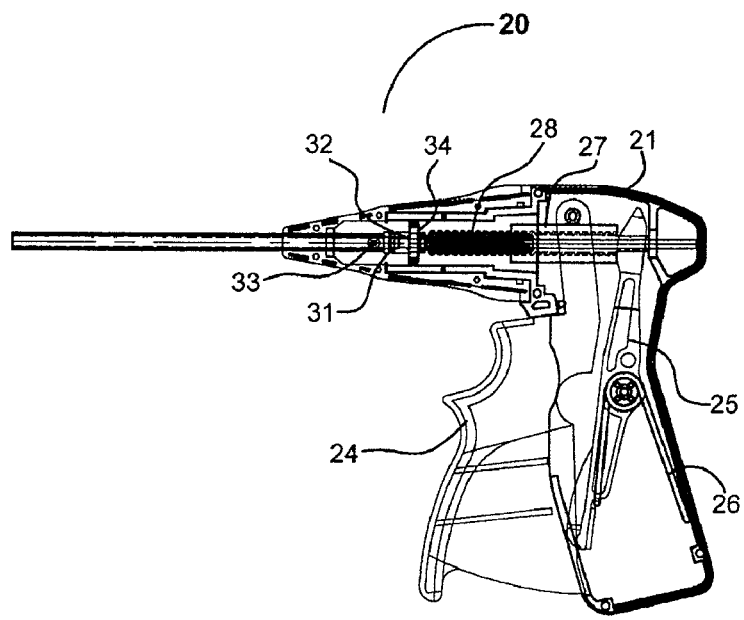
FIG. 5 is a cutaway view of the proximal end of the applier according to the present invention.
Figure 6:
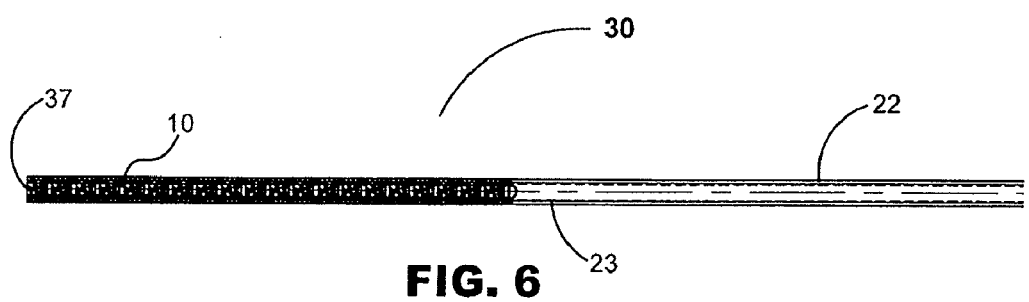
FIG. 6 is a cutaway view of the distal end of the applier according to the present invention.
Figure 7:
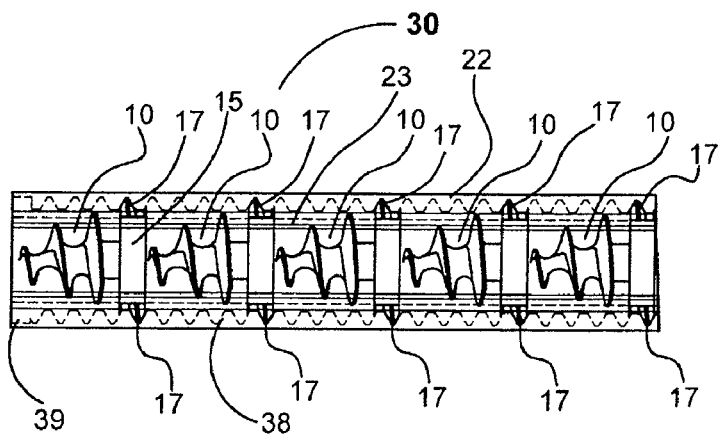
FIG. 7 is an enlargement of a cutaway view of the distal end of the applier according to the present invention.
Figure 8:
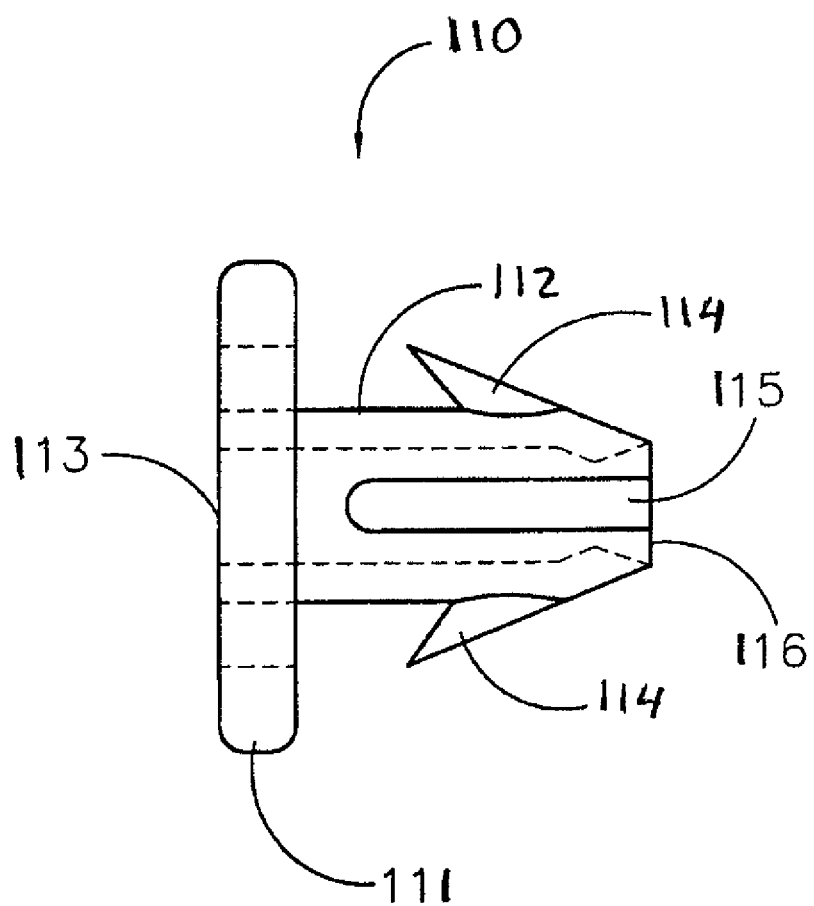
FIG. 8 is a side view of another surgical anchor of the present invention.
Figure 8:
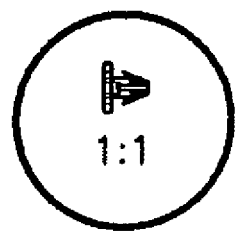

Turning now to FIGS. 5, 6, and 7 depicting the delivery device, or applier, for mesh anchor 10, generally designated as 20. FIG. 5 is a cutaway view of the proximal or handle end of applier 20. The proximal end of applier 20 comprises handle 21, outer tube 22, inner tube 23, trigger 24, actuator 25, return spring 26, helix nut 27, helix 28, clutch pin 31, clutch 32 clutch engager 34, and outer tube pins 33. FIG. 6 depicts the distal end 30 of applier 20 with twenty anchors 10 loaded ready for use. FIG. 7 is cutaway view of an enlargement of the distal end 30 of applier 20 depicting the distal most five anchors 10. Head threads 17 of anchors 10 engage internal screw threads 38 in outer tube 22. The distal end of inner tube 23 is slotted to accept multiple anchors 10 leaving two tines and two slots, not shown because of the cutaway. The two tines engage slots 15 in anchors 10 and head threads 17 extend through the inner tube slots 16 to engage outer tube threads 38. Rotation of inner tube 23 about its longitudinal axis rotates anchors 10 and advances them distally owing to head threads 17 engagement with outer tube threads 38. In the preferred embodiment anchors 10 are not in forced engagement with each other to avoid damage to distal tip 14 of anchors 10.

In a preferred embodiment there are twenty-four tube threads 38 per inch, the overall length of anchor 10 is 0.203 inches, with five full turns of inner tube 23 advancing anchors 10 0.208 inches. The distal end of outer tube 22 comprises counter bored 39 that preferably has a depth of 0.030 inches, which allows distal most anchor 10 to release from outer tube threads 38 in the last three quarters of a turn of a five turn actuation sequence in the application and ejection process, as will be detailed below.

Five embodiments of anchor 10 are described herein comprising four different molar ratios of DLPL and PG. The resins of the co-polymers in each case were prepared using well-known techniques of polymerization of cyclic dimmers. The molar percentages (M) of DLPL and PG were measured along with the residual monomer percentage (RM). After polymerization the resins were thoroughly dried. Anchor 10 was then injection molded in a standard micro-molding machine at 150 Deg. C. The transition glass temperature (Tg), the absorption time at 37 Deg. C. (to 20% of the original mass) (AT), the tensile strength (TS) and Young's modulus (YM) were then measured. Anchor 10 was then subjected to 25 kgy E Beam radiation and the tensile strength and Young's modulus re-measured. Standard techniques, well known by those skilled in the art, were employed in the measurements of each of the parameters. The results are shown below:

| Case I Parameter | | | | | | |
|---|---|---|---|---|---|---|
| M, DLPL, % | M, PG, % | RM, % | Tg, Deg. C. | AT, Months | TS, PSI | YN, PSI |
| 100 | 0 | 2.1 | 49.4 | 13 | 6100 | 206,000 |

| Case II Parameter | | | | | | |
|---|---|---|---|---|---|---|
| M, DLPL, % | M, PG, % | RM, % | Tg, Deg. C. | AT, Months | TS, PSI | YN, PSI |
| 85 | 15 | 2.1 | 49.7 | 5.8 | 7900 | 198,000 |

| Case III Parameter | | | | | | |
|---|---|---|---|---|---|---|
| M, DLPL, % | M, PG, % | RM, % | Tg, Deg. C. | AT, Months | TS, PSI | YN, PSI |
| 75 | 25 | 1.6 | 49.1 | 4.3 | 7200 | 192,000 |

| Case IV Parameter | | | | | | |
|---|---|---|---|---|---|---|
| M, DLPL, % | M, PG, % | RM, % | Tg, Deg. C. | AT, Months | TS, PSI | YN, PSI |
| 65 | 35 | 1.9 | 47.2 | 3.2 | 7400 | 190,000 |

| Case V Parameter | | | | | | |
|---|---|---|---|---|---|---|
| M, DLPL, % | M, PG, % | RM, % | Tg, Deg. C. | AT, Months | TS, PSI | YN, PSI |
| 52 | 48 | 1.2 | 46.7 | 1.5 | 8100 | 188,000 |

In each case retesting the tensile strength and Young's modulus after subjecting the anchor 10 to 25 kgy E Beam radiation yielded results statistically indistinguishable from the values in the tables above.

To design an appropriate insulated shipping container the historical average daily temperatures over a "hot weather route" from Florida to Arizona were obtained from www.engr.udayton.edu/weather. Heat flux data were determined from the historical data resulting in an insulation requirement of 2.5 inches of Cellofoam (a registered trademark of Cellofoam of North America, Inc.) with a thermal R-value of 3.86 per inch of thickness. Anchors 10 were then shipped over the route packed in the insulated container and the internal temperature of a un-air conditioned cargo space of a roadway common carrier was measured during a five-day trip from Jacksonville Fla. to Phoenix Ariz. from Sep. 9 till Sep. 14, 2004. The internal temperatures of the cargo space, Tc, and the internal temperature of the insulated container, Ti, containing anchors 10 were recorded every 30 minutes. The minimum and maximum temperatures in the cargo space and the insulated container are shown below:

| | Day 1 | Day 2 | Day 3 | Day 4 | Day 5 |
|---|---|---|---|---|---|
| Maximum Tc Deg. C. | 37 | 34 | 29 | 48 | 50 |
| Minimum Tc Deg. C. | 24 | 18 | 15 | 27 | 27 |
| Maximum Ti Temperature, Deg. C. | 27 | 27 | 26 | 27 | 27 |
| Minimum Ti Temperature, Deg. C. | 24 | 26 | 21 | 24 | 24 |

Thus it is seen from the data above that the insulated shipping container is adequate for maintaining anchor 10 temperatures well below the glass transition temperature of 49 Deg. C. of the preferred co-polymer, 75/25 DLPL/PG, Case III above.

The preferred embodiment for the current invention is an injection molded anchor as depicted in FIG. 1 comprising 75% DLPL, 25% PG, sterilized with radiation, either gamma or E Beam, at 25 kgy and packaged first in a hermetically sealed pack and an insulated shipping container.

Applier Loading and Operation

Multiple anchors 10 are loaded onto the tines of inner tube 23 head to tail with tips 14 pointed distally. Anchors 10 are rotationally orientated such that the tines of inner tube 23 engage head slots 16. The proximal end of the loaded inner tube assembly is inserted into the distal end of outer tube 22 until proximal-most anchor 10 encounters outer tube threads 38. The inner tube assembly is then rotated until the distal end of inner tube 23 is flush with or slightly recessed into outer tube 22. In this position the proximal end of inner tube 23 is proximal of the proximal end of outer tube 22. Near the proximal end of inner tube 23 a drill through hole perpendicular to the longitudinal axis is located to accept clutch pin 31 for securing clutch 32 to inner tube 23. The inner and outer tube and clutch assembly is then affixed into handle 21 with outer tube pins 33 (one from each side) which allows for inner tube 23 to rotate inside outer tube 22.

The loaded applier 20 is placed into a surgical field, usually through a 5 mm trocar, and the distal end of applier 20 is held firmly against mesh 52, which covers tissue 51. Outer tube threads 38 act as a force reactor to counter the distal force, generated by the screw-in process of the threaded tissue-snaring section 13, so that anchors 10 are unable to move proximally. Outer tube threads 38 engaging head threads 17 also restrain anchors 10 from falling out of the distal end of applier 20 under the influence of gravity, for example.

Trigger 24 is then squeezed rotating actuator 25 against helix nut 27. Helix nut 27 and helix 28 are design according to well-known art such that the force applied to helix nut 27 causes helix nut 27 to move distally and rotate helix 28 in a right-hand manner when helix nut 27 and helix 28 are threaded in a left hand manner. The primary design consideration is the coefficient of static friction (COSF) between helix nut 27 and helix 28 for a given helix thread pitch. According to well-known art there exists a critical value of COSF for a given pitch above which the system is self-locking and below which helix nut 27 linear movement causes helix 28 to rotate. In the preferred embodiment the system comprises a left hand double helix with a pitch of 0.100 inches, lead of 0.200 inches and COSF less than 0.2 and preferably less than 0.15. One inch distal movement of helix nut 27 causes helix 28 and clutch engager 34 to make five full revolutions. Clutch 32 is designed such that as helix 28 and hence clutch engager 34 rotate in a right-hand sense inner tube 23 rotates five full turns in a right-hand sense. As explained above rotation of inner tube 23 rotates anchors 10. Tip 14 of distal most-anchor 10 engages and penetrates mesh 52 and threaded tissue-snaring section 13 screws into and draws tissue 51 and mesh 52 together. During the last three quarters of a rotation of the five revolutions head threads 17 of distal most anchor 10 enter into counter bore 39. Removal of the distal end 30 of applier 20 from mesh 52 releases distal-most anchor 10 and ejects it from applier 20. Mesh 52 is thus affixed to tissue 51. After the anchor screw-in process is complete trigger 24 is released, reset spring 26 returns actuator 25 to its start, or home, position. This returns helix nut 37 proximally since it is attached to actuator 25. As helix nut 37 returns proximal helix 28 and clutch engager 34 rotates in the left-hand sense. Clutch 31 is detached from the rotation owing to the clutch design, thus inner tube 23 does not rotate during the reset process leaving the stack of anchors 10 forward in the same position as before, less distal-most anchor 10. Applier 20 is fully reset and ready for the deployment of the next anchor 10.

Turning now to FIGS. 8-18, the present invention also relates to a surgical device and, more particularly, to a surgical device for serially deploying at least one surgical anchor from a surgical device to attach a prosthesis in place in the repair of a defect in tissue such as an inguinal hernia.

The embodiment illustrated in FIGS. 8-18 of the present invention is illustrated and described in conjunction with a repair of an inguinal hernia, by way of example, however, it should be understood that the present invention is applicable to various other surgical procedures that require the repair of defects in tissue.

The Anchor

Figure 9:
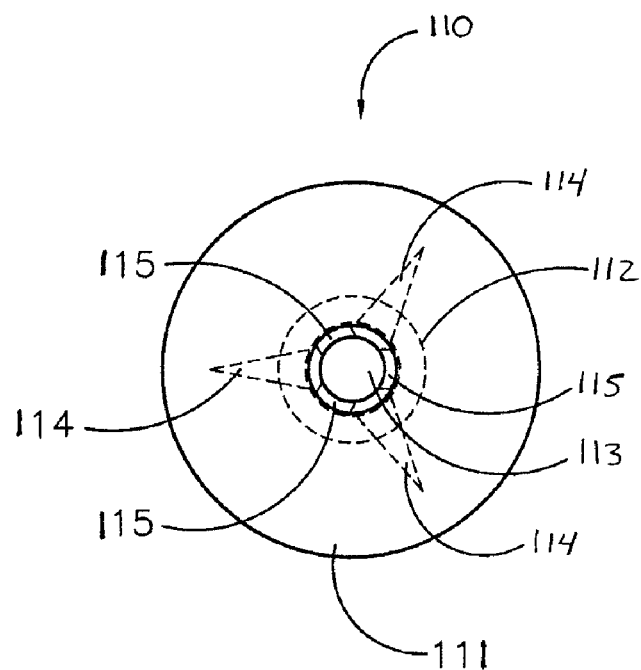
FIG. 9 is the distal end view of the surgical anchor of FIG. 8.
Figure 10:
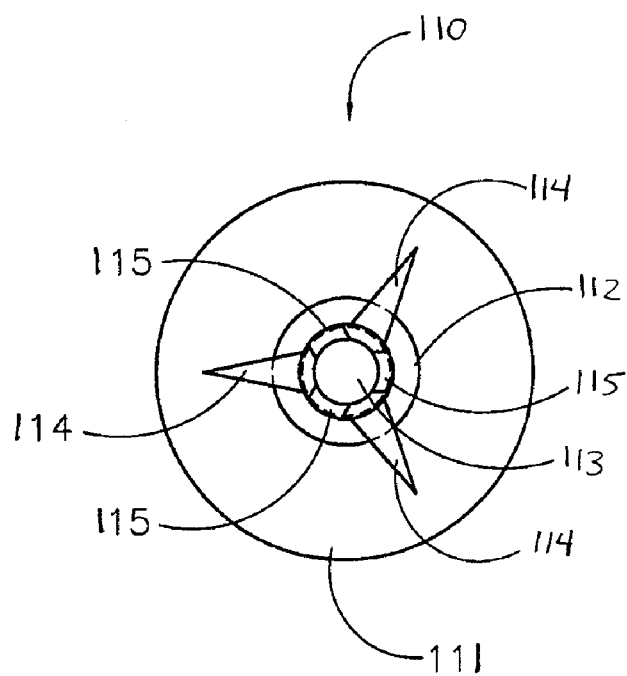
FIG. 10 is the proximal end view of the surgical anchor of FIG. 8.

Referring to FIGS. 7, 9, and 10, the anchor of the present invention is generally designated by the number 110. Anchor 110 comprises a penetration shaft section 112, a head 111, and three rigid barbs 114. Internal channel 113 is concentric with the longitudinal axis and three slits 115 are equally spaced around penetration shaft 112. The distal end of anchor 110 is designated 116. Penetration shaft 112 is tapered from the distal most point on barbs 114 to distal end 116. Distal end 116 is blunt. Anchor 110 is preferably formed from a bio-absorbable material that has a lifetime after implantation of from 2 to 12 months. Barbs 114 are rigid and are formed integral to the penetration shaft 114. Slits 115 in distal end 116 of penetration shaft 112 allow distal end 116 to flex to facilitate ejection of anchor 110 from the delivery device, which is described in more detail below. The general dimensions of the anchor are: head diameter, 5 mm; penetration shaft diameter 3 mm; overall length 5 mm.

The Delivery Device

Figure 11:
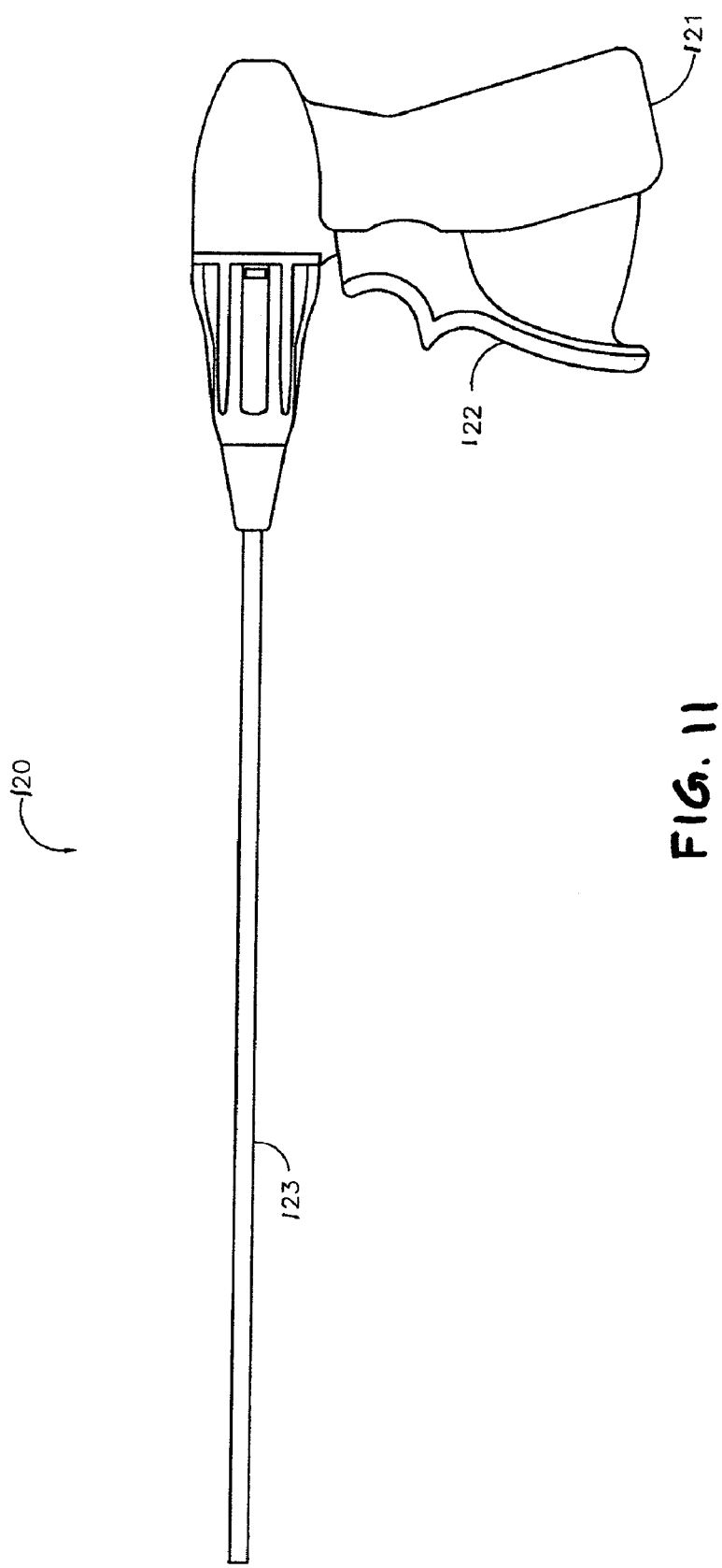
FIG. 11 is a side view of an anchor delivery device of the present invention for firing the surgical anchor of FIGS. 8-10.
Figure 12:
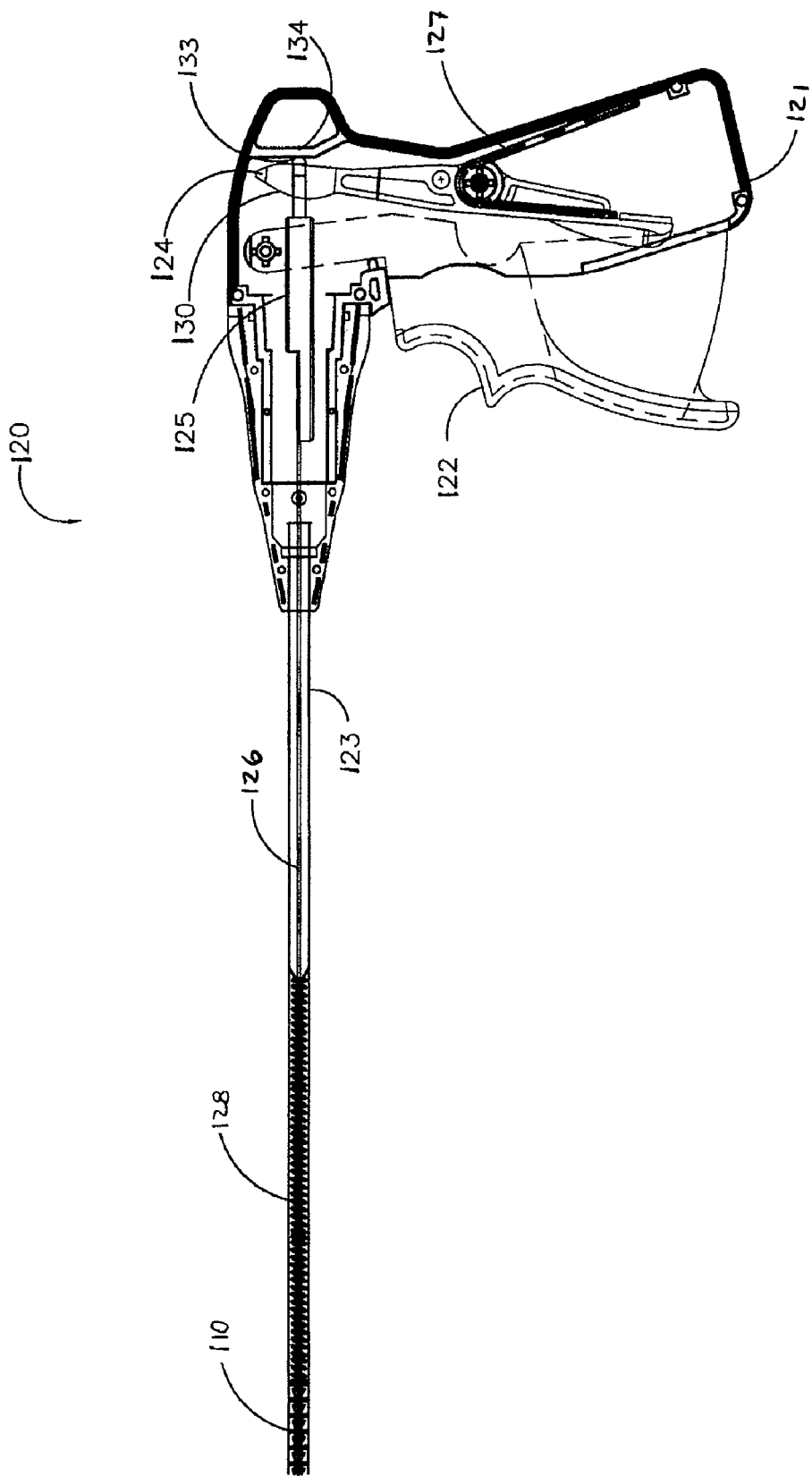
FIG. 12 is a cross section of the anchor delivery device of FIG. 11 in the home state.

The deliver device can be best understood by referring to FIGS. 11-15. FIG. 11 depicts a side view of the delivery device, generally designated with the number 120. Delivery device 120 comprises pistol grip handle 121, an actuator or trigger 122 and delivery tube 123. The outside diameter of delivery tube 123 is, preferably, approximately 5 mm for use with standard trocars, laparoscopic devices for minimally invasive entry into the abdomen. Handle 121 and trigger 122 are preferably formed from plastic material such as ABS or polycarbonate but alternately can be formed from metal to facilitate reuse and re-sterilization. Delivery tube 123 is preferably formed from thin wall stainless steel but can alternately be formed from rigid biocompatible plastic material. As can be seen in FIG. 12 delivery tube 123 contains multiple anchors 110. Delivery tube 123 can be designed so that it is readily detachable from handle 121 thus resulting in a reusable handle and a reloadable or replaceable tube, otherwise the entire delivery device is for use only in a single surgical procedure.

Figure 14:
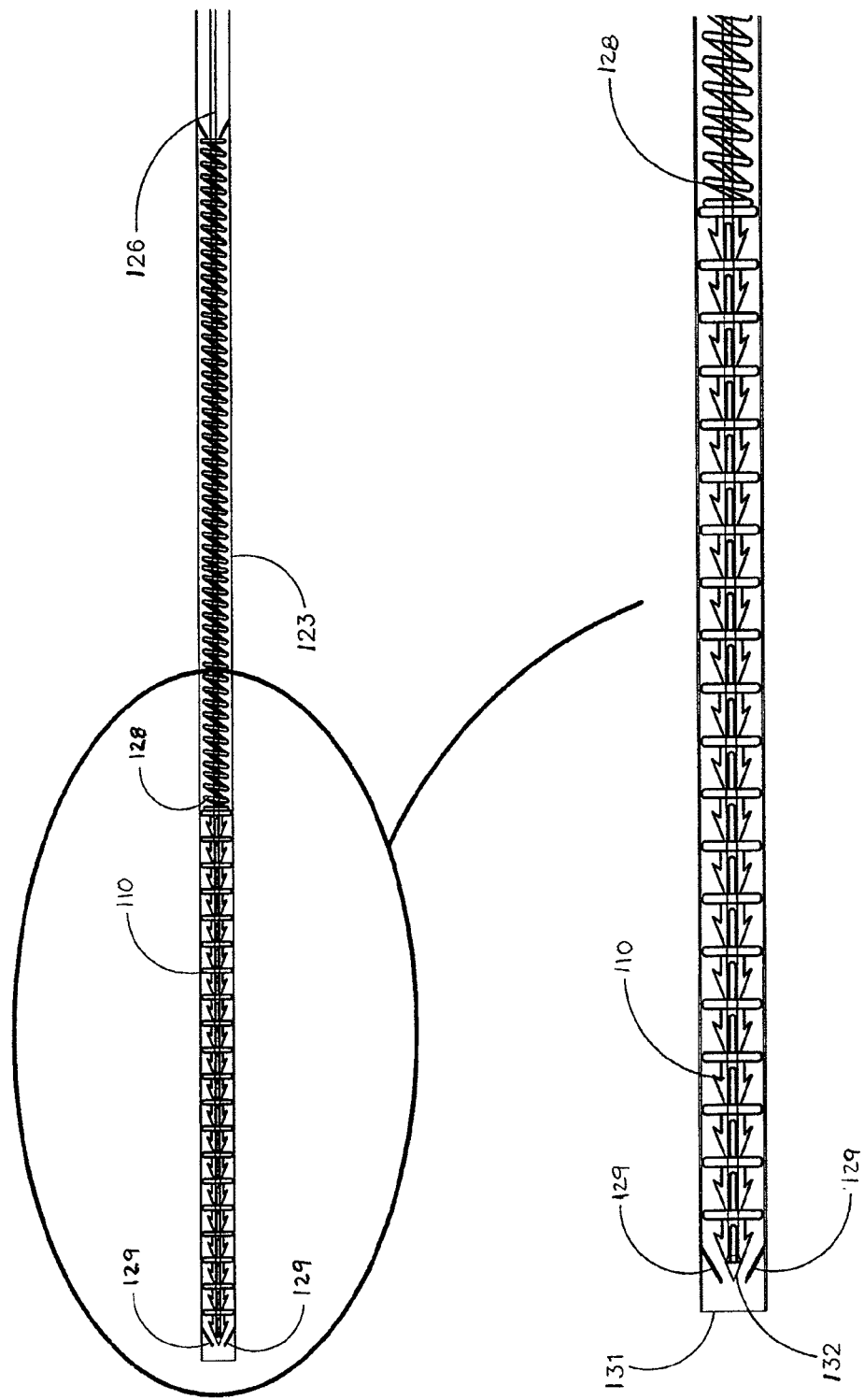
FIG. 14 is a cross section of the distal end of the delivery device of FIG. 11 in the home state.

FIGS. 12 and 14 are longitudinal cross sections of the proximal and distal ends respectively of delivery device 120 in the home or equilibrium state. Trigger 122 abuts rotating lever 124 which is spring loaded with torsion spring 127. Anchor carrier 126, connected proximally to piston 125, comprises a cylindrical rod terminating distally in tissue penetrator member or tissue penetrator 132. Anchors carrier 126 is fed inside internal channels 113 of anchors 110 such that anchors 110 are in head 111 to distal end 116-contact such that distal ends 116 of anchors 110 are aligned toward distal end 131 of delivery device 120. The proximal end of queuing spring 128 is fixed with respect to delivery tube 123 and the distal end of queuing spring 128 abuts head 111 of proximal-most anchor 110. Queuing spring 128 is compressed and serves to urge anchors 110 distally against each other and against the proximal shoulder of tissue penetrator 132 that abuts distal end 116 of distal-most anchor 10 and provides a counter force against queuing spring 128. Distal end 116 of anchor 110 and the proximal end of tissue penetrator 132 are each formed such that there is a smooth transition between the two components. This minimizes the insertion force required to set anchor 110 into the prosthesis and tissue. With anchor carrier 126 fully loaded with a plurality of anchors the reaction force of queuing spring 128 is sized such that it is inadequate to spread slots 115 of distal most-anchor 110. This assures containment of distal-most anchor 110 inside delivery tube 123 when delivery device 120 is in the home state as depicted in FIGS. 12 and 14.

Figure 13:
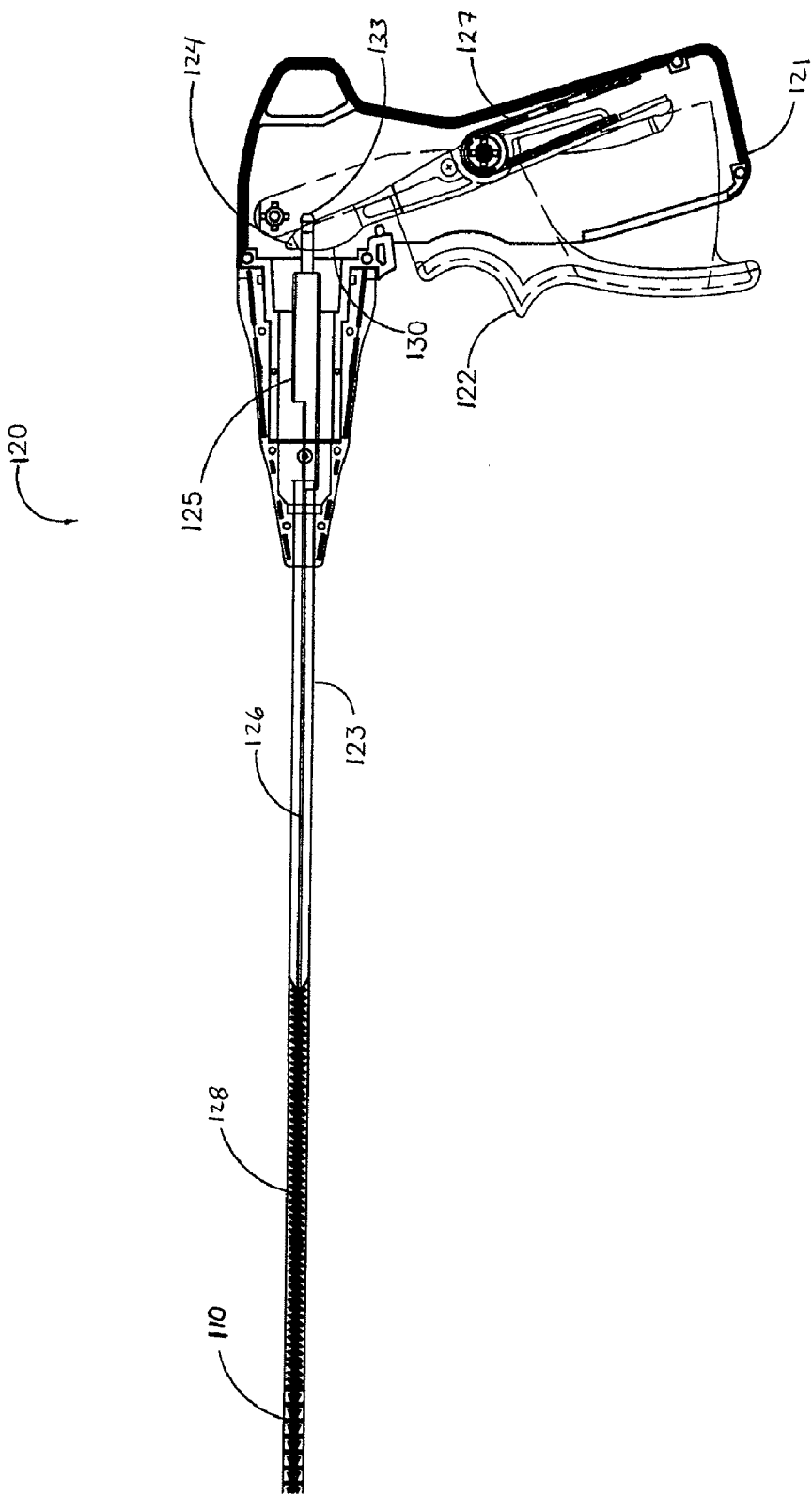
FIG. 13 is a cross section of the anchor delivery device of FIG. 11 in the stroked state.
Figure 15:
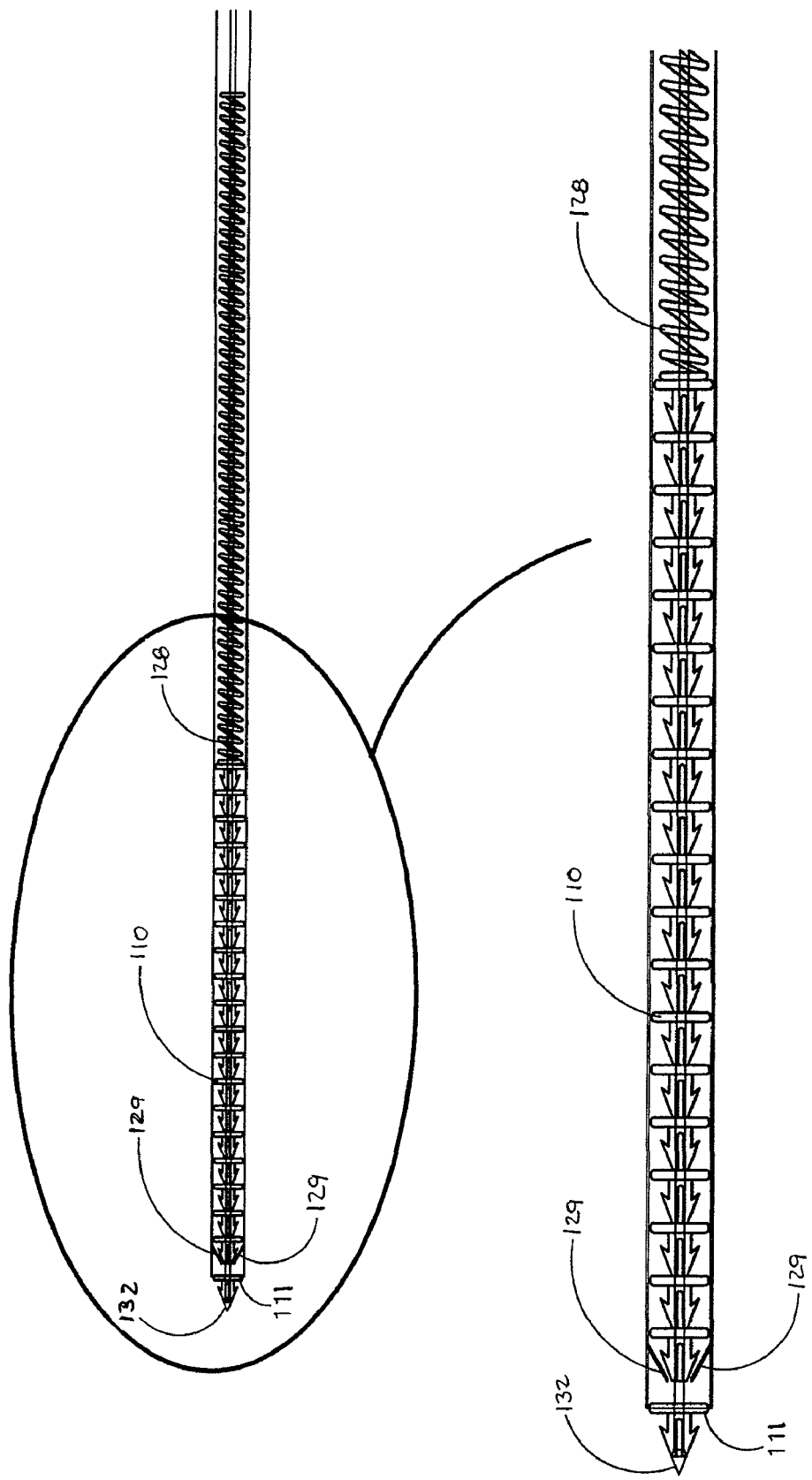
FIG. 15 is a cross section of the distal end of the delivery device of FIG. 11 in the stroked state.

Referring now to FIGS. 13 and 15, when the surgeon pulls trigger 122 proximally, away from the home state, lever 124 rotates counterclockwise such that cam surface 130 of lever 124 contacts piston 125 which drives anchor carrier rod 126 distally. Torsion spring 127 compresses as lever 124 is rotated counterclockwise. Anchor carrier 126 is urged distally within the inside diameter of queuing spring 128. FIGS. 13 and 15 depict delivery device 120 in the fully stroked state. In this state head 111 of distal-most anchor 110 has been urged past flexible reaction members 129 that are fixed with respect to delivery tube 123 and penetration shaft 112 of distal-most anchor 110 is exposed past the distal end 131 of delivery tube 123. In this fully stroked state trigger 122 is locked to handle 121 by the surgeon's closed hand and no further activation of deliver device 120 is necessary to set the anchor into the prosthesis and tissue. Thus no countervailing dynamic forces are required from a single hand of the surgeon. Simply the surgeon gently pushing the entire assembly distally then sets distal-most anchor 110. Tissue penetrator 132 leads distal-most anchor 110 into the prosthesis and the tissue until penetration shaft 112 fully engages and head 111 stops against the prosthesis. Flexible reaction members 129 counter the insertion force of distal-most anchor 110 so that anchors 110 do not move proximal during insertion.

Barbs 114 lock distal-most anchor 110 into the tissue. Distal-most anchor 110 is then ejected from delivery device 120 when the surgeon retracts delivery device 120 proximally. Slits 115 spread open allowing penetrator 132 to pass through internal channel 113, thus releasing distal-most anchor 110 from delivery device 120. Trigger 122 is then released. Torsion spring 127 rotates lever 124 clockwise and pulls piston 125 and anchor carrier 126 proximal owing to piston proximal member 133. Handle stop 134 defines the proximal position of piston 125 and anchor carrier 126 in the home state. Delivery device 120 is now reset to the home state and ready to deploy the next anchor 110.

The Method

Figure 16:
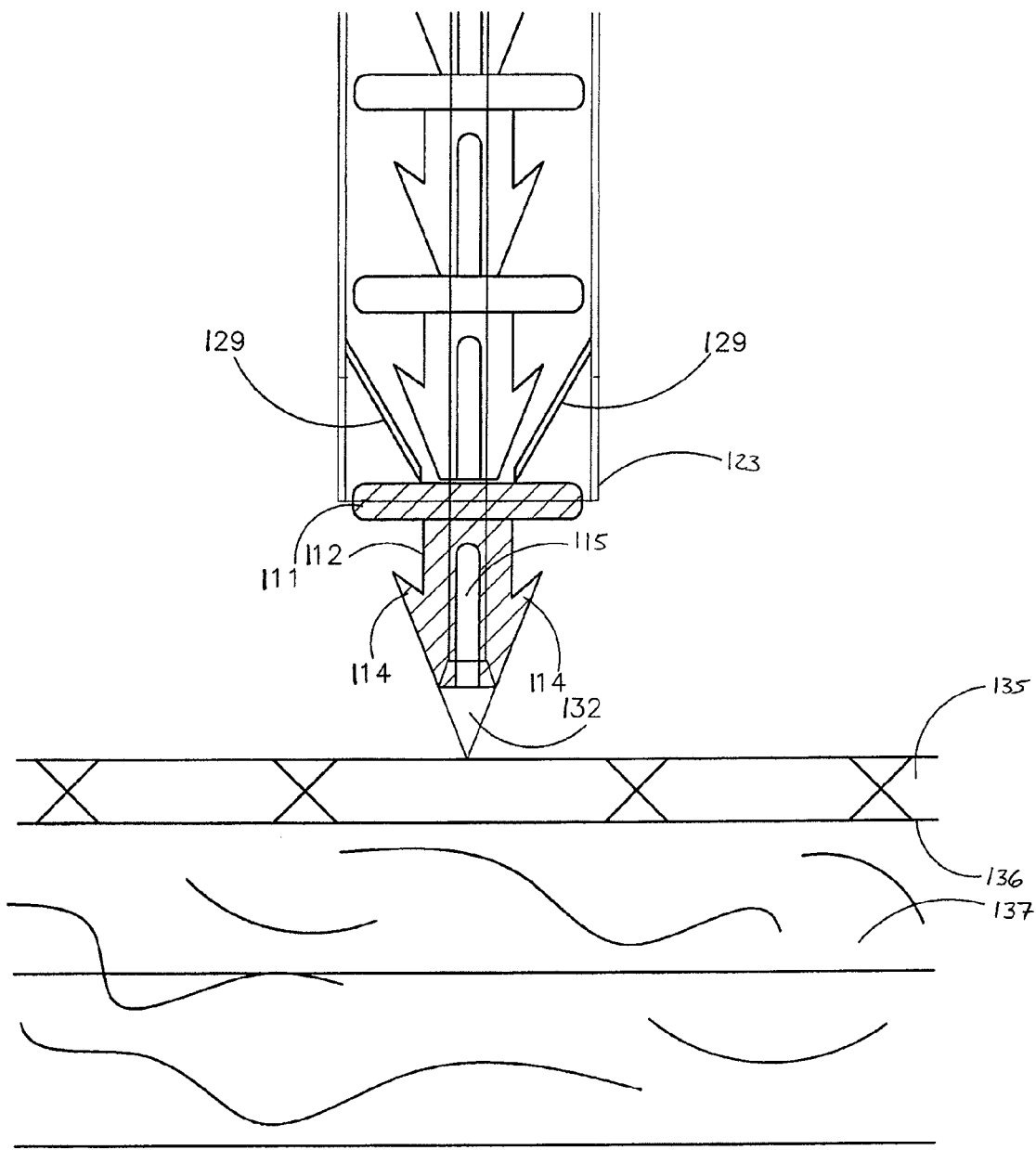
FIG. 16 depicts the deliver device of FIG. 11 in the stroked state proximate the mesh.
Figure 17:
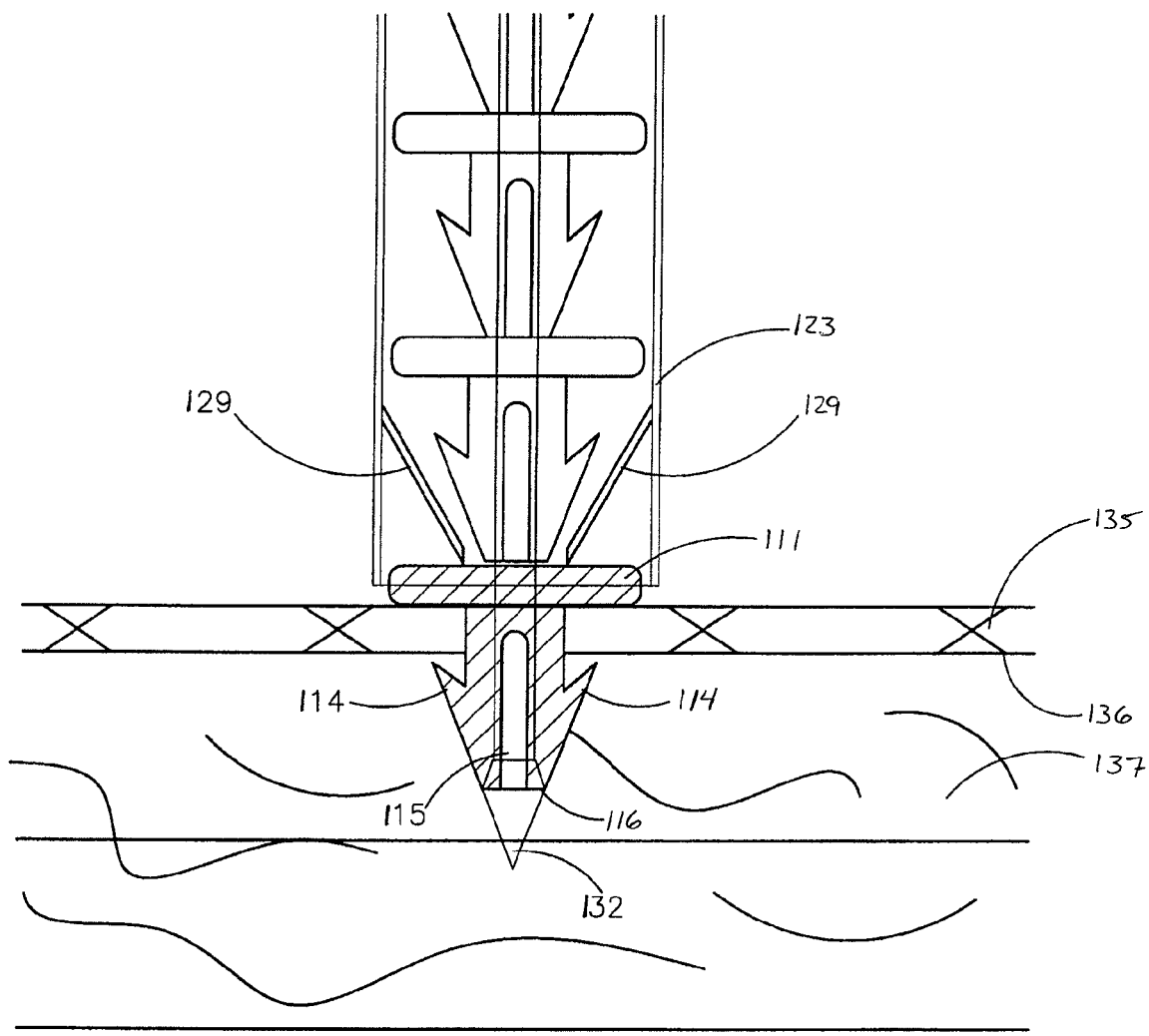
FIG. 17 shows the anchor of FIGS. 8-10 after penetration prior to release of the trigger of the delivery device of FIG. 11.
Figure 18:
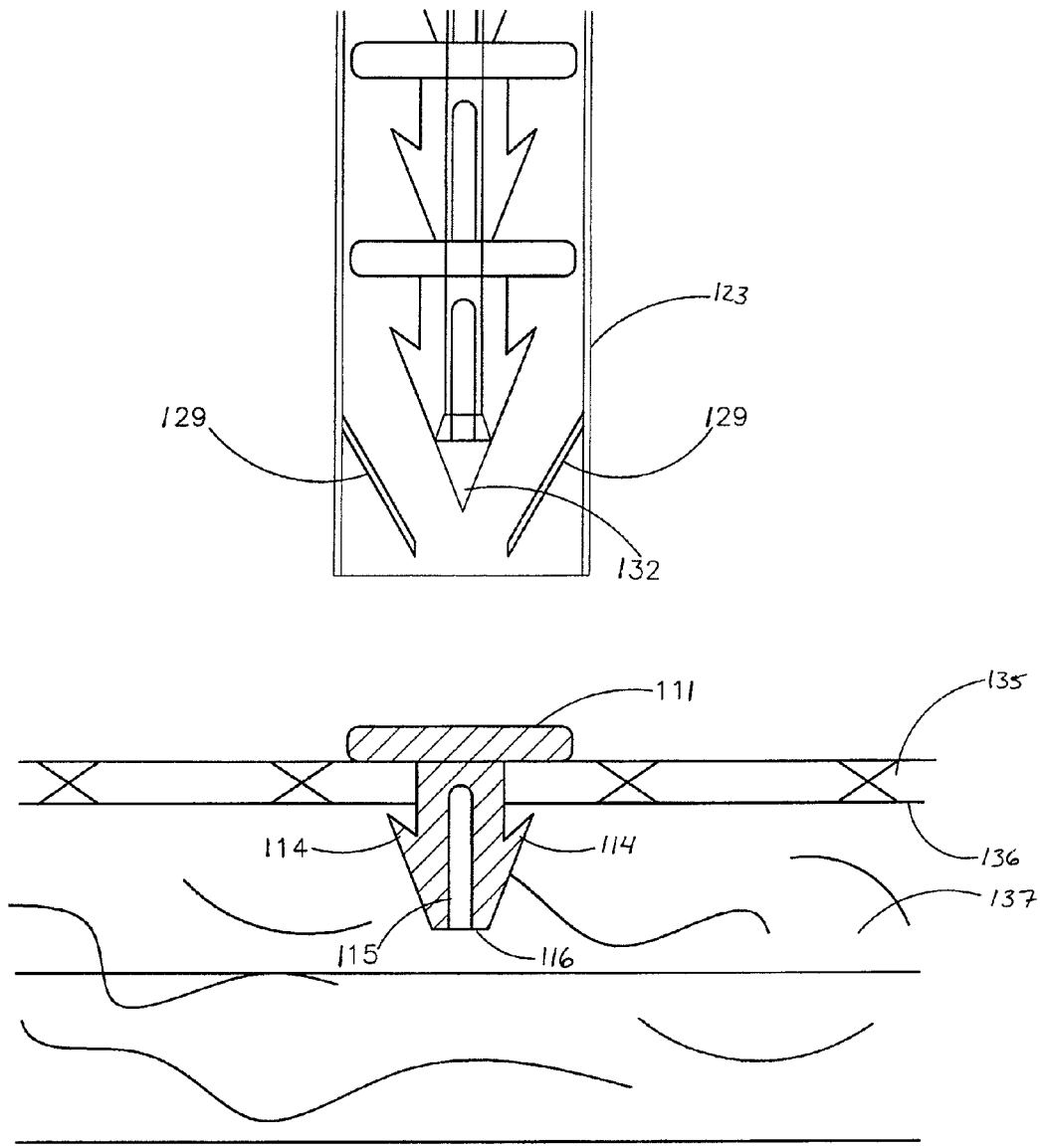
FIG. 18 shows the deployed anchor of FIGS. 8-10 after ejection from the delivery device of FIG. 11.

FIGS. 16-18 illustrate the method of use of the delivery device 120 and anchor 110. These longitudinal cross-sectional views of the distal end of delivery tube 123 show the steps involved in using delivery device 120 and anchor 110 for securing mesh to the inguinal floor, for example. For clarity only distal-most anchor 110 is shown crosshatched. FIG. 16 depicts the distal end of the delivery device 120 proximate mesh 135, which covers the inguinal floor 136 and underlying tissue 137. Delivery device 120 is in the fully stroked state as seen shown in detail in FIGS. 13 and 15. The surgeon has pulled trigger 122 fully proximal exposing penetrator 132, barbs 114, and penetration shaft 112 distally from delivery tube 123. The surgeon then urges the entire assembly forward so that penetrator 132 and penetration shaft 112 have penetrated mesh 135 and into tissue 137 as seen in FIG. 17. The surgeon moves delivery device 120 proximally and withdraws delivery device 110 from contact with mesh 135. Barbs 114 provide a counter force in the tissue so that anchor 110 remains in the tissue. Distal end 116 of deployed anchor 110 is flexed open owning to the counter force to torsion spring 127 so that penetrator 132 and anchor carrier 126 are allowed to move proximally through internal channel 113 of distal-most anchor 110. The surgeon then releases trigger 122. Torsion spring 127 causes lever 124 to rotate clockwise which moves piston 125 and anchor carrier 126 proximally to the home position as described above.

The proximal shoulder of penetrator 132 then nests against the next distal-most anchor so that delivery device 120 is reset to the home position and is ready for deploying another anchor 110.

Figure 19:
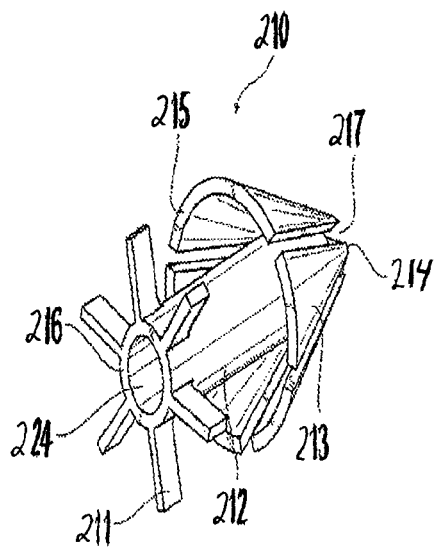
FIG. 19 is an isometric view of an anchor according to another embodiment of the present invention.
Figure 20:
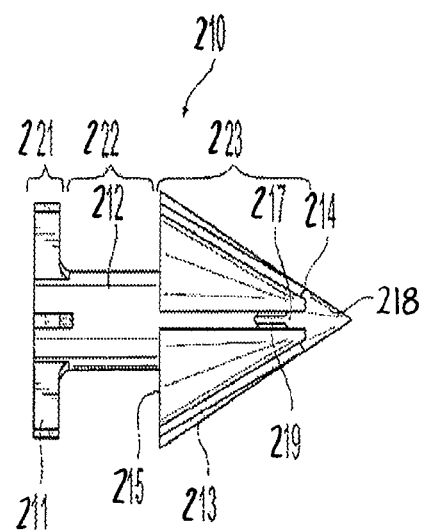
FIG. 20 is a side view of the anchor of FIG. 19.

Turning now to FIG. 19 through FIG. 22, depictions of an anchor according to another embodiment of the current invention is generally designated as 210. Anchor 210 comprises three sections, head section 221, mesh-tissue section 222, and tissue snaring section 223. Head section 221 comprises six spokes 211 attached to hub 216. Throughhole 224 is formed parallel with the longitudinal axis of anchor 210. Distal features described above in relation to anchor 110, within through hole 224, serve to restrain anchor 210 distally when anchor 210 comes into contact with tissue penetrator 218 of the delivery device. Head section 221 can alternately be a solid or slotted disk but the spoke arrangement as shown in FIG. 19 aids in injection molding anchor 210 without the need for movable slides in the mold. In either configuration the head section 221 acts to restrain mesh 225 against tissue 226. Mesh-tissue section 212 is generally cylindrical shaped with a dimension transverse to its longitudinal axis that is smaller than the transverse dimension of head 221 and the transverse dimension of tissue snaring section 223. The mesh-tissue section serves to contain the interface of mesh 25 and tissue 226. Owing to the elasticity of tissue 226 upon penetration it is well known that tissue will contract around mesh-tissue section 222 such that tissue 226 will come into contact with the outer wall 212 of mesh-tissue section 222. Tissue snaring section 223 comprises six tissue snares 213 that serve to restrain anchor 210 when anchor 210 is subjected to proximal forces that tend to expel anchor 210 proximally, opposite the direction of tissue penetrator 218. Tissue penetrator 218 is connected to rod 219 that is connected to an actuator in the delivery device as described in detail above. Tissue penetrator 218 attached to rod 219, preferably formed from medical grade stainless steel, serves two purposes. Tissue penetrator 218 acts to provide a lead-in for anchor 210 for penetrating mesh 225 and tissue 226 and both tissue penetrator 218 and rod 219 provide added columnar strength to anchor 210. After anchor 210 is set into tissue 226 tissue penetrator 218 and rod 219 are retracted by the actuator mechanism of the delivery device as described above. Snares 213 comprise distal ends 214 that smoothly interfaces with tissue penetrator 218 as described above. Proximal edges 215 of snares 213 are angled with respect to the longitudinal axis of anchor 210 such that under the influence of proximal forces the transverse dimension of tissue snaring section 223 tends to increase. This serves to increase the fixation strength of anchor 210 in tissue 226. The distal end of tissue snaring section 223 is outwardly expandable owing to six slots 217 that allow for retraction of tissue penetrator 218 after anchor 210 is imbedded in tissue 226.

Figure 21:
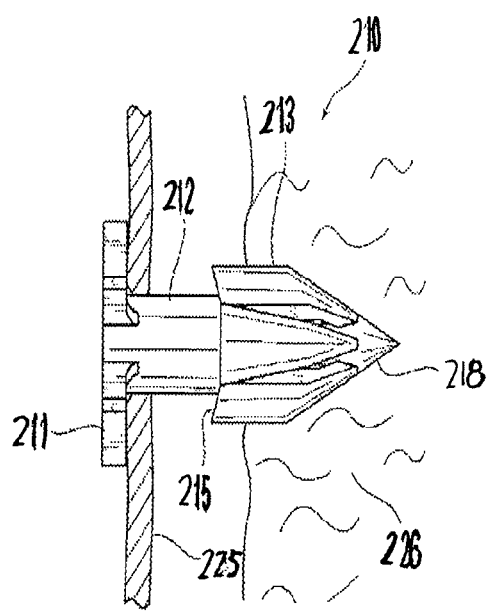
FIG. 21 is a side view of the anchor of FIGS. 19 and 20 as it passes through tissue.

As can be seen in FIG. 21, unlike the anchor 110 described above, tissue-snaring section 223 is flexible such that snares 213 bend inward toward mesh-tissue outer wall 212 under the radial force of mesh 225 and tissue 226 during penetration. This minimizes the penetration hole diameter in mesh 225 and tissue 226.

Figure 22:
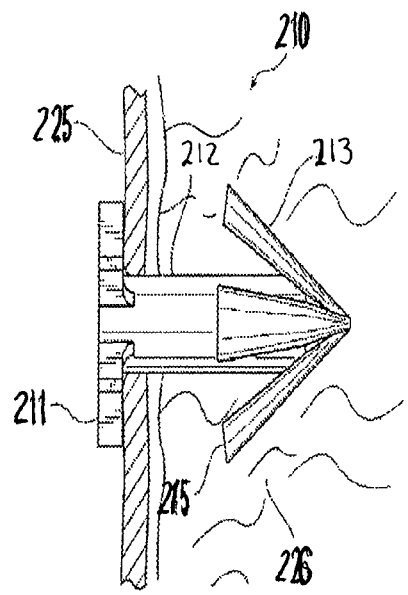
FIG. 22 is a side view of the anchor of FIGS. 19 and 20 under an expelling force.

FIG. 22 depicts anchor 210 after tissue penetrator 218 has been retracted and with anchor 210 under the influence of a proximal force caused by an increase in intra-abdominal pressure (IAP), for example. In this incidence the transverse dimension of tissue snaring section 223 increases, as shown in FIG. 22, such that the fixation strength of anchor 210 increases.

From the foregoing, it will be appreciated that the absorbable anchor of the present invention functions to securely fasten tough, non macro-porous, and relative inelastic mesh to tissue. The anchor of the present invention will disintegrate after the body has secured the mesh against migration and contraction. The absorbable anchor of the present invention can be sterilized so that mechanical properties are maintained and it can be shipped under severe temperature conditions with insulated packaging so that the glass transition temperature is not exceeded. It will also be appreciated that the absorbable anchor of the present invention may be utilized in a number of applications such as hernia repair, bladder neck suspension, and implant drug delivery systems.

While several particular forms of the invention have been illustrated and described, it will be apparent by those skilled in the art that other modifications are within the scope and spirit of the present disclosure.

What is claimed:

1. A delivery device for delivering at least one surgical anchor into a patient's tissue, the delivery device comprising:
   a. a housing;
   b. a delivery tube with distal and proximal ends, the delivery tube including a retention member disposed at the distal end thereof and extending inwardly at an angle transverse with respect to a longitudinal axis of the delivery tube; and
   c. a reciprocating anchor carrier with distal and proximal positions and distal and proximal ends, the distal end of the anchor carrier terminating in a tissue penetrator member, the anchor carrier being moveable distally and proximally with respect to the delivery device, the tissue penetrator member defining an annular shoulder configured to removably retain a plurality of surgical anchors about the anchor carrier.

2. The device of claim 1, wherein the delivery device includes a plurality of surgical anchors, wherein each of the plurality of surgical anchors are located radially about the anchor carrier, each surgical anchor having a penetration section and a head section.

3. The device of claim 1, wherein the delivery device includes a plurality of surgical anchors, wherein each of the plurality of surgical anchors includes a blunt distal end.

4. The device of claim 1, wherein the delivery device includes a plurality of surgical anchors, wherein each of the plurality of surgical anchors includes one or more barbs for engagement with the tissue.

5. The device of claim 1, wherein the delivery device includes a plurality of surgical anchors, wherein each of the plurality of surgical anchors includes one or more slits to allow the surgical anchor to flex open.

6. The device of claim 5, wherein the one or more slits extend proximally from the distal end of the surgical anchor to allow the distal end of the surgical anchor to flex to facilitate removal of the surgical anchor from the anchor carrier.

7. The device of claim 1, wherein the annular shoulder defines an outer diameter that is substantially similar to an outer diameter defined by a distal end of the surgical anchor.

8. The device of claim 1, wherein the delivery device includes a plurality of surgical anchors, wherein each of the plurality of surgical anchors defines an internal channel, the internal channel having a constricted section along a longitudinal length of the surgical anchor.

9. The device of claim 1, wherein the tissue penetrating member and a distal portion of a distal-most surgical anchor is configured to provide a substantially smooth transition between the tissue penetrating member and the distal portion of the distal-most surgical anchor.

10. The device of claim 1, wherein the annular shoulder tapers inward from the tissue penetrating member to the anchor carrier.

11. The device of claim 1, wherein proximal movement of the annular shoulder provides a flexing force to open a distal end of a distal-most surgical fastener.

* * * * *